United States Patent [19]

Turková et al.

[11] Patent Number: 4,613,502

[45] Date of Patent: Sep. 23, 1986

[54] PROTEOLYTIC, DRY BIOPOLYMERIC COMPOSITION FOR TREATMENT OF WOUNDS, AND METHOD OF USING SAME

[75] Inventors: Jaroslava Turková, Česk Brod; Jiří Stamberg, Prague, both of Czechoslovakia

[73] Assignee: Ceskoslovenska akademie ved, Czechoslovakia

[21] Appl. No.: 679,118

[22] Filed: Dec. 6, 1984

[30] Foreign Application Priority Data

Dec. 8, 1983 [CS] Czechoslovakia ............... 9180-83
Dec. 8, 1983 [CS] Czechoslovakia ............... 9181-83

[51] Int. Cl.$^4$ .................... A61K 37/48; A61K 37/547
[52] U.S. Cl. ........................ 424/94; 424/16; 514/55; 514/59
[58] Field of Search ............ 424/94, 16; 514/55, 514/59

[56] References Cited

U.S. PATENT DOCUMENTS

| | | | |
|---|---|---|---|
| 2,908,614 | 10/1959 | Muggleton et al. | 424/94 |
| 2,997,423 | 8/1961 | Novak | 514/59 |
| 3,003,917 | 10/1961 | Beiler et al. | 424/94 |
| 3,914,413 | 10/1975 | Balassa | 514/55 |
| 3,940,478 | 2/1976 | Kurtz | 424/94 |
| 4,242,219 | 12/1980 | Bogerman et al. | 424/94 |
| 4,361,551 | 11/1982 | Galbraith | 424/94 |

OTHER PUBLICATIONS

Nozawa et al., Chem. Abst., vol. 96 (1982), p. 195855v.

*Primary Examiner*—Sam Rosen
*Attorney, Agent, or Firm*—Leydig, Voit & Mayer, Ltd.

[57] ABSTRACT

The invention pertains to a cover of wounds in the form of a powder or a dry powdery fluid and is useful in covering and treating of ulcerous and necrotic wounds. It consists of animal or fungous chitin and chitosan in a powdered form of particle size 0.01 to 0.3 mm or of crosslinked dextran in the form of spheric particles of diameter 0.05 to 0.5 mm and of an immobilized protease. Enzymes are chemically bonded to the structure of the biopolymeric carrier and provide cleaning of the wound by dissolution of undesirable protein material, in particular fibrin, necrotic tissues, components of pus, and the like. In addition the adsorption and regeneration effects of powder act to provide suction of exudate and purulent matter infected with bacteria into interstitial capillary space. The cover according to the invention acts by fast cleaning of necrotic defects and speeds up the granulation and healing of the wound. The invention can be utilized in pharmaceutical production.

5 Claims, No Drawings

PROTEOLYTIC, DRY BIOPOLYMERIC COMPOSITION FOR TREATMENT OF WOUNDS, AND METHOD OF USING SAME

This invention pertains to a proteolytic cover of wounds consisting of particles based on polysaccharides to which an enzyme of protease type is bonded after activation. The cover for wounds of a biopolymer type in the form of powder or a dry powdery fluid is used for covering and treatment of ulcerous and necrotic wounds.

In addition to classic bicomponent powders based, for example, on talc or starch and sulfonamide, antibiotics, or antimycotics as an active compound, various biopolymeric powdery covers of wounds are recently recommended. These new preparations employ above all an adsorption or proteolytic principle or a combination of both principles. The adsorption effect consists in suction of liquid components of purulent matter and the proteolytic effect consists in enzymatic decomposition of undesirable proteins in the exudate. Biopolymeric covers of the above mentioned type were described, for example, by B. S. Jacobsson et al. in Scand. J. Plast. Reconstr. Surg. 10, 65–72 (1976), by H. Dautzenberg et al. in Czechoslovak Patent Application No. PV 4129-82, and by J. Turková et al. in Czechoslovak Patent Application No. PV 7138-83, on which U.S. Ser. No. 654,632 is based.

An important type of biopolymeric powder are the preparations based on hydrophilic biopolymers. Their main advantage is insolubility in water, which prevents contamination of the wound with foreign components. The biopolymeric hydrophilic insoluble powders are well tolerated by organisms because they do not exhibit side effects. Their effect consists in the interaction between the solid and liquid phases, i.e. between the powder particles and the liquid component of the wound. This interaction is limited to the region of contact and is not transferred to other places or organism. Two kinds of biopolymeric covers of wounds can be distinguished according to the type of interaction—the adsorption and proteolytic covers. The former act physically, the latter chemically.

For example, spherical crosslinked dextran, which is sold under the name Debrisan® (product of Pharmacia, Uppsala, Sweden) is an effective adsorption cover (see also B. S. Jacobsson et al.; Scand. J. Plast. Reconstr. Surg. 10, 65 (1976)).

The proteolytic cover based on spherical cellusose with covalently bonded proteases and dried by lyophilization and its application in medical practice was described by J. Turková et al. in the Czechoslovak Patent Application No. PV 7138-83.

Both types of biopolymeric covers have advantages in comparison with classic powders hitherto used, but also have some limitations. The above mentioned dextrane adsorption cover acts only physically, i.e. by suction of water and aqueous solutions or dispersions into the porous material of the particles and the interstitial space of powder layer. The cellulose proteolytic cover acts above all enzymatically, but its parallel suction of liquid components from the wound, i.e. the adsorption or adsorption effect, is highly desirable. The later effect can be, however, obtained only by special provisions during the preparation of the cellulose carrier and the cover, which are often complicated and costly.

Cellulose tends naturally to crystallization during drying and to the formation of structures with a low porosity. If covers with a high adsorption capacity (high porosity) are to be obtained, special drying procedures should be used in all stages of preparation.

Another important type of biopolymeric powders are the preparations based on chitin, which have been described by L. L. Balassa in several patents (Ger. No. 1,906,155 (1969); Ger. No. 1,906,159 (1970); Brit. No. 1,252,373 (1971); U.S. Pat. No. 3,632,754 (1972); U.S. Pat. No. 3,914,413 (1975)). The chitin powder acts on a completely different base than the above mentioned biopolymeric types; its effect can be indicated as regeneration. Chitin very slowly depolymerizes in a wound and its monomeric components efficiently enter into metabolic reactions in the wound. The chitin powder contributes in this way to the regeneration of damaged skin tissues.

The limitation of chitin powders consists in their specific action, i.e. in the regeneration principle. Chitin is marked by its high crystallinity and the corresponding low porosity of the material, so that the powders based on chitin have only a small adsorption effect. The proteolytic principle of wound cleaning does not apply in the recent chitin powders at all.

The above mentioned shortcomings of hydrophilic insoluble biopolymeric and chitin covers are removed in a cover according to the invention.

The invention pertains to a cover of wounds consisting of spheric particles based on polysaccharides, to which an enzyme of protease type is bonded after activation, whereas the said polysaccharides are compounds selected from the group comprising crosslinked dextran, chitin, and chitosan.

The cover of wounds according to the invention based on dextrane consists of spheric particles of diameter 0.05–0.5 mm.

The cover of wounds according to the invention based on chitin and chitosan consists of particles of size 0.01–0.3 mm.

A marked feature of the new cover is application of crosslinked dextran as a biopolymeric phase for immobilization of proteases. Unlike cellulose, the crosslinked dextran exhibits a high porosity without requiring special provisions. The porous structure of the dextran carrier can be controlled within broad limits by the degree of crosslinking of the initial polymer. In contrast to cellulose, the porosity is not lost during drying of the crosslinked dextran which has been swollen in water, and a product which swells again to a high water content can be obtained by common drying methods. Thus, covers according to the invention, which are based on dextran, have a high adsorption capacity in addition to the proteolytic effect, without requiring special provisions.

To prepare the cover of the new type, spheric crosslinked dextrans of particle size 0.05–0.5 mm are used, which swell in water so as to contain 2–10 g water per g of dry substance (the content of water in the swollen material being determined after centrifugation on a glass filter). These requirements are met in the commercial product Debrisan® and the corresponding chromatographic material available under the trade mark Sephadex® from the same producer, or corresponding materials of other origin.

The porous crosslinked dextrans have a convenient chemical reactivity for bonding of enzymes, and known or modified procedures may be used for the immobilization of proteases (see, e.g., Handbook of Enzyme Biotechnology, Alan Wiseman, Editor, E. Horwood, London 1975). The procedures chosen should provide products with firmly bonded enzymes which are not released during application. The product is advantageously dried by lyophilization.

With covers based on chitin and chitosan, an alkaline treatment of the chitin dust obtained by grinding and classification of chitin of animal or fungous origin is carried out before immobilization, which leads to a partial deacetylation of N-acetylglucosamine structural units and liberation of ionogenic amine groups. Chitosan structural units are introduced into the chitin structure in this way. The presence of primary amino groups in the polymer structure considerably enhances the chemical reactivity of biopolymer in the activation for protease bonding. The immobilization can proceed by known methods described, for example, by W. L. Standley, et al. (Biotechnol. Bioeng. 17, 315 (1975); U.S. Pat. No. 3,909,358 (1975)) or R. A. A. Muzzarelli et al. (Chitin, Pergamon Press, Oxford 1977, p.199).

The regeneration effect typical for chitin powders is retained also in the new type of biopolymeric cover. A relatively low degree of substitution of structural units, which is necessary for immobilization of proteases, and achievement of the desirable enzymatic activity means that a large portion of unchanged structural units remains in the structure of the biopolymer, and said structural units can be released by a slow enzymatic depolymerization and contribute in the regeneration of skin tissues. In fresh and old healing wounds, a sufficient amount of lysozyme is present, which enzymatically cleaves the chitin structures. The released monomer units take part in the metabolism of hexosamines and orientate and crosslink collagen. It is also known that uridine diphospho-N-acetylglucosamine is a key compound in the biosynthesis of chondroitin sulfates, hyaluronic acid and glycoproteins. These processes accompany recovery of skin tissues.

With regard to this mechanism, fine fractions of powder down to 0.01 mm can also be advantageously used without danger of their penetration into blood circulation.

Application of the new cover in medical practice is similar to that described in Czechoslovak Patent Application No. PV 7138-83.

The following examples illustrate the method for preparing covers according to the invention. However, the scope of the invention is not limited thereby.

EXAMPLE 1

Preparation of the cover with immobilized chymotrypsin

Crosslinked dextran of trade mark Sephadex G-100 (produced by Pharmacia, Uppsala, Sweden) with spheric particles of diameter 0.05–0.5 mm was used as a carrier and 2-amino-4,6-dichloro-s-triazine was used for its activation. The crosslinked dextran was swelled in water in an amount corresponding to 7.5 g dry substance. The activation agent was dissolved in 750 ml acetone at 50° C. and diluted with the same volume of water at this temperature. The crosslinked dextran was stirred with 300 ml activation solution for 5 min at 50° C. A solution prepared by mixing 15 g sodium carbonate in 100 ml water with 60 ml 1M hydrochloric acod (HCl) was added in the amount of 120 ml (50° C.) to the activation mixture, which was then stirred at 50° C. for another 5 min. Hydrochloric acid (HCl) was added to decrease the pH of the activation mixture abruptly below 7, and the activated product was filtered, washed with 50% aqueous acetone and water, and stored in 0.1M phosphate buffer at pH 6.6 and 2° C.

Chymotrypsin was immobilized on the activated carrier from a 1.5% solution in 0.2M borate buffer of pH 8.75 at 24° C. After 12 hours, 195 mg enzyme was immobilized per g of carrier. The crosslinked dextran with bonded chymotrypsin was alternately washed with 0.1M borate buffer containing 1 mol sodium chloride (NaCl)/l (pH 8) and 0.1M acetate buffer containing 1 mol NaCl/l (pH 4.5) until the proteolytic activity zero of the eluate was attained. The sample was eventually washed with 0.25M borate buffer (pH 8) and lyophilized.

EXAMPLE 2

Preparation of the cover with immobilized papain

Crosslinked dextran of trade mark Debrisan ® (produced by Pharmacia, Uppsala, Sweden) with the spheric particles of diameter 0.05–0.5 mm, which was activated by introducing imidocarbonate groups, was used as a carrier.

The crosslinked dextran (1 g) was activated by contact with cyanogen bromide (40 ml) at 24° C. and pH 11 for 6 min. The product was then washed with a cold 0.1M solution of sodium hydrogen carbonate (NaHCO₃) (500 ml) for 7 min, water and 0.1M phosphate buffer of pH 7.6.

Papain was bonded on the activated carrier from a 0.1M phosphate buffer of pH 7.6 at ambient temperature for 16 hours.

The product was eventually worked in the similar way as in Example 1, i.e. it was perfectly washed by alternating the buffers until the eluate did not exhibit the proteolytic activity and dried by lyophilization.

EXAMPLE 3

Preparation of the cover with immobilized trypsin

Crosslinked dextran of trade mark Sephadex G 50 (produced by Pharmacia, Uppsala, Sweden) with spheric particles of diameter 0.05–0.5 mm, which was activated by introducing isothiocyanate groups with thiophosgene, was used as a carrier.

The crosslinked dextran (20 g) was stirred with 4-nitrophenyl glycidyl ether (4 g) in 20 ml toluene and a solution of sodium hydrozide (80 ml) was added. The suspension was heated to 70° C. for 18 hours. The carrier was washed and swelled in 100 ml water, 40 ml 5M NaOH and 2 g solium dithionite was added and the reaction mixture was heated to 65° C. for 1 hour. The product was washed, swelled in 3.5M phosphate buffer (pH 6.8), reacted with 10% solution of thiophosgene in tetrachloromethane, washed and dried.

Trypsin was bonded on the activated carrier from its 1.8% solution in 0.05M borate buffer of pH 8.6 at 5° C. under an atmosphere of nitrogen. After 15 hours, 200 mg enzyme per g carrier was immobilized.

The product was washed as in Example 1 by alternating the buffers until the proteolytic activity zero was attained in the eluate, saturated with the same borate buffer and lyophilized.

EXAMPLE 4

Preparation of the cover from animal chitin

Chitin isolated from crab shells and processed by grinding and classification to particle size 0.05–0.15 mm (100 g) was stirred with 2 liters 40% NaOH at 115° C. for 6 hours under a nitrogen atmosphere. The reaction mixture was cooled, the product was filtered and washed with water to neutral reaction. Chitin was deacylated from about 70% under these conditions.

The hydrolyzed product in the amount corresponding to 15 g substance was packed into a column and eluted with a phosphate buffer of pH 8.5 until the eluate attained the pH value of the eluating buffer. A mixture of 15 ml above buffer, 15 ml chymotrypsin solution (containing 0.1 g chymotrypsin) and 15 ml 4% aqueous glutaraldehyde was poured on the column, allowed to flow slowly through the bed and then allowed to stand in the column for 1 hour. On completion of immobilization, the bed was washed with 500 ml above used buffer and then alternately with alkaline and acid buffers (i.e. with 0.1M borate buffer of pH 9 containing 1 mol NaCl/l and 0.1M acetate buffer of pH 4.5 containing 1 mol NaCL/l) to elute perfectly the unbonded enzyme. The washing was continued until the proteolytic activity zero of eluate was achieved. The product was eventually washed with 0.25M borate buffer of pH 8 and lyophilized from suspension in this buffer.

EXAMPLE 5

Preparation of the cover from fungous chitin

Mycelium of fungus *Penicilium chrysogenum*, which is a waste material from production of peniciin, was used for the preparation of the cover. The mycelar material was sterilized and freed of lipid components, in particular fats, by extraction with chloroform at ambient temperature. The resulting product was mixed with 1M NaOH at ambient temperature for 18 hours, acidified with HCl and refined by dialysis. The chitinous material was wet-ground to particle size 0.05–0.8 mm. The hydrolysis, immobilization and final processing were carried out in the same way as in Example 4.

The invention also comprises the method of treating an exudative wound by applying to the surface of the wound one or more of the compositions described above in general and more particularly in Examples 1 through 5.

We claim as our invention:

1. A proteolytic, dry, biopolymeric composition for treatment of exudative wounds which comprises small substantially spherical particles of a polysaccharide from the group consisting of crosslinked dextran, chitin and chitosan having bonded thereto an immobilized protease enzyme in an amount sufficient to cause enzymatic decomposition of undesirable proteins in the wound exudate.

2. The composition of claim 1 wherein the spherical particles have a diameter between 0.01 mm and 0.5 mm.

3. The composition of claim 1 wherein the particles are a crosslinked dextran having a diameter of 0.05 mm to 0.5 mm.

4. The composition of claim 1 wherein the particles are chitin having a diameter of 0.01 mm to 0.3 mm.

5. The method of treating an exudative wound which comprises applying to the surface of said wound the composition set forth in claim 1.

* * * * *